United States Patent [19]

Boggs et al.

[11] Patent Number: 5,358,705
[45] Date of Patent: Oct. 25, 1994

[54] USE OF N-ACETYLATED AMINO ACID COMPLEXES IN ORAL CARE COMPOSITIONS

[75] Inventors: Robert W. Boggs, Cincinnati; John R. Wietfeldt, Wyoming, both of Ohio

[73] Assignee: The Procter & Gamble Company, Cincinnati, Ohio

[21] Appl. No.: 154,841

[22] Filed: Nov. 19, 1993

Related U.S. Application Data

[62] Division of Ser. No. 905,963, Jun. 29, 1992, Pat. No. 5,286,480.

[51] Int. Cl.⁵ .......................... A61K 7/16; A61K 7/22
[52] U.S. Cl. .......................................... 424/54; 424/49
[58] Field of Search ...................................... 424/49–58

[56] References Cited

U.S. PATENT DOCUMENTS

| | | | |
|---|---|---|---|
| 3,787,466 | 1/1974 | Kagawa et al. | 260/448 |
| 3,991,178 | 11/1976 | Humbert et al. | 424/54 |
| 4,092,410 | 5/1978 | Ogata et al. | 424/78 |
| 4,164,570 | 8/1979 | Clough et al. | 424/175 |
| 4,314,991 | 2/1982 | Sipos | 424/56 |
| 4,339,378 | 7/1982 | Masaki et al. | 260/112.5 |
| 4,339,379 | 7/1982 | Masaki et al. | 260/112.5 |
| 4,342,774 | 8/1982 | Okabe et al. | 424/273 |
| 4,379,177 | 4/1983 | McCoy et al. | 426/656 |
| 4,486,403 | 12/1984 | Mechanic et al. | 424/54 |
| 4,670,403 | 6/1987 | Ishida et al. | 436/90 |
| 4,772,470 | 9/1988 | Inoue et al. | 424/435 |
| 4,976,954 | 12/1990 | Kleber et al. | 424/52 |
| 5,017,364 | 5/1991 | Mitsutake et al. | 424/54 |
| 5,028,412 | 7/1991 | Putt et al. | 424/48 |
| 5,061,729 | 10/1991 | Kincses et al. | 514/562 |
| 5,064,640 | 11/1991 | Kleber et al. | 424/52 |
| 5,080,906 | 1/1992 | Carenzi et al. | 424/452 |

FOREIGN PATENT DOCUMENTS

| | | | |
|---|---|---|---|
| 0391629 | 10/1990 | European Pat. Off. | C07K 7/08 |
| 0465921A1 | 1/1992 | European Pat. Off. | A23G 3/30 |
| 2755124 | 6/1979 | Fed. Rep. of Germany | C12K 1/10 |
| 8178370 | 5/1937 | France . | |
| 20970790 | 3/1972 | France | A61K 27/00 |
| 2233607A | 9/1990 | Japan | A61K 7/18 |
| 3200714A | 9/1991 | Japan | A61K 7/16 |
| WO89/07932 | 9/1989 | PCT Int'l Appl. | A61K 7/16 |
| WO9102530A | 3/1991 | PCT Int'l Appl. | A61K 31/70 |
| WO91/15204 | 10/1991 | PCT Int'l Appl. | A61K 31/195 |
| 490384 | 8/1938 | United Kingdom . | |
| 1168302 | 10/1969 | United Kingdom | C07C 103/46 |

OTHER PUBLICATIONS

Hay, D. I., R. J. Gibbons, S. K. Schluckebier, M. S. Gerland, & D. H. Schlesinger, "A Sequence in Salivary Acidic Proline-Rich Proteins which Mediated Adhesion of Actinomyces Viscosus LY7 to Hydroxyapatite", *J. Dent. Res.*, vol. 69, p. 268, Abstract No. 1278 (Feb. 1990).

"Aluminum Aceglutamide", *Drugs of Today*, vol. XIV, No. 2, pp. 53–56 (month unknown 1978).

"N-Acetyl Amino Acid Aluminum Salts", *Chemical Abstracts*, 94:175554b Nov. 1980.

*Primary Examiner*—Shep K. Rose
*Attorney, Agent, or Firm*—J. R. Crosmun; M. B. Graff; D. L. Suter

[57] ABSTRACT

The subject invention encompasses methods and compositions comprising N-acetylated amino acid complexes for reducing or preventing dental plaque, calculus, or gingival or periodontol diseases of the oral cavity in humans or lower animals.

20 Claims, No Drawings

USE OF N-ACETYLATED AMINO ACID COMPLEXES IN ORAL CARE COMPOSITIONS

This is a division of application Ser. No. 07/905,963, filed on Jun. 29, 1992, now U.S. Pat. No. 5,286,480.

TECHNICAL FIELD

The subject invention relates to oral compositions used for the prevention of accumulation of plaque and calculus on teeth.

BACKGROUND OF THE INVENTION

Dental plaque is a non-calcified accumulation primarily comprising oral microorganisms and their products. Within a few hours after teeth cleaning, a film of salivary mucus, consisting primarily of proteins, forms a pellicle on the teeth. Various oral bacteria colonize the mucus and multiply, forming a layer of plaque. Carbohydrate food debris adhere to the mucus and are digested by some types of plaque causing bacteria. The digestion produces by-products which add to the plaque and produces acid which erodes tooth enamel. The plaque adheres tenaciously to the teeth and is not easily dislodged. Depending on bacterial activity and environmental factors, plaque may lead to caries or inflammatory changes in tissue adjacent to plaque coated teeth.

If not prevented or removed, plaque may become embedded with mineral salts, containing calcium and phosphate, to form a hard crusty deposit, calculus or tartar, on the teeth. Calculus may be white or yellowish in color or may be stained or discolored by extraneous agents. Calculus tends to be more unsightly than plaque and much more difficult to remove from the teeth. The toxins in plaque and calculus can irritate the gingival tissues surrounding the coated teeth, causing inflammation and destruction of the gums which can lead to other complications.

It is an object of the subject invention to provide compositions for impeding plaque accumulation.

SUMMARY OF THE INVENTION

The subject invention encompasses compositions for reducing or preventing dental plaque, or gingival or periodontal diseases, of the oral cavity in humans or lower animals comprising a safe and effective amount of a complex of metal ion with N-acetylated amino acid wherein the metal ion is selected from the group consisting of $In^{3+}$, $Ga^{3+}$, and $Al^{3+}$; and a pharmaceutically-acceptable carrier.

DETAILED DESCRIPTION OF THE INVENTION

The compositions of the subject invention comprise a complex of a metal ion with one or more N-acetylated amino acids in a pharmaceutically-acceptable topical oral carrier.

"Pharmaceutically-acceptable topical oral carrier", as used herein, denotes a carrier for the active compound or compounds of the subject invention (hereinafter "Active" or "Actives") comprising solid or liquid filler diluents suitable for use in contact with the oral tissues of humans and lower animals without undue toxicity, incompatibility, instability, irritation, allergic response, and the like, commensurate with a reasonable benefit/risk ratio. Such topical oral carrier, when combined with an Active, results in a composition which is administered topically to the oral cavity. Preferably such compositions are held in the oral cavity for a period of time, and then largely expectorated rather than being swallowed. Such compositions include mouthwashes, mouth rinses, mouth sprays, dental treatment solutions, toothpastes, dental gels, tooth powders, prophylaxis pastes, lozenges, chewing gums and the like and are more fully described hereinafter. Dentifrices and mouthwashes are the preferred compositions.

By the term "metal ion", as used herein, is meant $Al^{3+}$, $Ga^{3+}$, or $In^{3+}$.

As used herein, "alkyl" means a carbon-containing chain which may be straight, branched, or cyclic; substituted (mono- or poly-) or unsubstituted; saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "amino acid" includes any naturally or non-naturally occurring, L- or D-configuration, preferably L-, organic acid having the structure

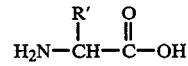

wherein—R′ is selected from the group consisting of hydrogen and alkyl having from about 1 to about 12 carbon atoms.

As used herein, amino acids include "naturally occurring amino acids" which are glycine, alanine, valine, isoleucine, leucine, phenylalanine, proline, methionine, serine, threonine, tyrosine, tryptophan, asparagine, glutamine, cysteine, aspartic acid, glutamic acid, lysine, arginine, and histidine.

As used herein, "N-acetylated amino acid" includes any amino acid substituted with an acetyl group as in the following structure:

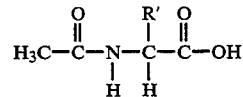

The Actives

The subject invention provides a plaque inhibiting composition comprising certain Actives which are complexes of metal ions with N-acetylated amino acids. The ratio of metal ion to N-acetylated amino acid is preferably from about 1:4 to about 1:1, more preferably from about 1:3 to about 1:1.

While not limited to such structures, the metal ion/N-acetylated amino acid complex is believed generally to conform to the following structure:

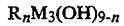

In the above structure, each M is independently a metal selected from the group consisting of indium, gallium, and aluminum. Preferred is all M being the same; more preferred is all M being aluminum.

In the above structure, each R is independently selected from N-acetylated amino acids. Preferably R is an N-acetylated naturally occurring amino acid; more preferably R is an N-acetylated naturally occurring L-amino acid; more preferably still R is N-acetyl-L- glutamine or N-acetyl-L-cysteine. Preferred is all R being the same.

In the above structure, n is an integer in the range of 3 to 9. Each metal ion in the Active must be bound to at least one N-acetylated amino acid, thus n must be at least 3. Preferably n is about 5.

An example of such an Active, N-acetyl-L-glutamine aluminum salts, is disclosed in U.S. Pat. No. 3,787,466 issued to Kagawa et al. on Jan. 22, 1974 and is incorporated by reference herein.

Mixtures of Actives may be used as the active agent in the compositions of the subject invention. For example, N-acetyl-L-glutamine aluminum salts may be combined with N-acetyl-L-glycine aluminum salts; N-acetyl-L-asparagine indium salts may be combined with N-acetyl-L-cysteine indium salts; N-acetyl-L-leucine gallium salts may be combined with N-acetyl-L-arginine aluminum salts. Such examples of mixtures are given here by way of example, and not for purposes of limitation.

The Actives of the subject invention are soluble in conventional oral care compositions, such as mouthwashes, mouth rinses, and toothpastes. However, oral care compositions of the subject invention should be substantially free from materials known to complex strongly with aluminum, gallium, or indium or to form insoluble precipitates with those metal ions. Materials to avoid include fluoride ions, phosphate ions, metal ion chelators such as ethylenediaminetetraacetic acid (EDTA) or nitrilotriacetic acid (NTA), and others. Inclusion of substantial quantities of these substances in a composition tends to negate the efficacy of the Actives and to reduce anti-plaque activity.

It has been unexpectedly found that treatment of teeth with Actives of the subject invention leads to a dramatic reduction in bacteria binding to the tooth surface. While the anti-plaque activity of the Actives is not limited by the following, it is believed that such activity is at least partially achieved in the manner described hereinbelow. The hydroxyapatite surfaces of teeth possess phosphate and calcium receptors. The Actives possessing metal ions of aluminum, gallium or indium bind to the phosphate receptors while displacing some or all of the N-acetylated amino acid components of the Actives. The N-acetylated amino acid component of the Active, being more weakly complexed to the metal ion, is displaced by the phosphate group attached to the hydroxyapatite surface. The result appears to be a metal phosphate coating on the hydroxyapatite surface. Hydroxy groups and water appear to be bound to the metal ions forming a hydrophilic hydrous gel layer. The gel layer inhibits bacteria from obtaining access and binding to saliva proteins in the pellicle on the tooth surface. Because bacteria are impeded from adhering to the teeth, fewer are present on the tooth surface to multiply. The result is a reduction in bacterial accumulation, therefore in plaque and gingivitis when used in the oral cavity.

Additionally, the Actives coagulate colloidal particles like bacteria. The hydrolized metal cations may attach to saliva proteins and bacteria. The decrease in electrostatic inter-bacterial repulsions may lead to the additional benefit of aiding in the aggregation and clearance of bacteria from the oral cavity.

Although other materials are known to prevent bacterial adhesion, most of these materials are polymers which can impart an unpleasant increase in mouth rinse viscosity when used at effective concentrations. The Actives of the subject invention, not being polymers, do not have this undesirable property. Additionally, the Actives are not easily displaced from the tooth surface by saliva. This allows treatment to persist longer than treatments using most other active compounds targeted at preventing adherence. Also, use of Actives of the subject invention avoids the unpleasant taste and staining characteristics of commonly used antimicrobials.

Compositions

Compositions of the subject invention preferably comprise aqueous solutions of Active. Such compositions typically comprise from about 0.05% to about 10% by weight, preferably from about 0.1% to about 5% by weight, and most preferably from about 0.5% to about 3% by weight of Active. For a mouth rinse formulation, the most preferred concentration of Active ranges from about 1% to about 2% by weight.

By "safe and effective amount" as used herein is meant an amount of compound or composition sufficient to induce a significant positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors.

By the term "comprising", as used herein, is meant that various additional components can be conjointly employed in the compositions of this invention.

Components of the topical, oral carrier are suitable for administration to the oral cavity of a human or lower animal and are compatible with one another and the other components, especially the Active, used in an oral composition of the subject invention. The term "compatible" as used herein, means that the components are capable of being co-mingled with one another, in a manner such that there is no interaction which would substantially reduce the efficacy of the oral composition under ordinary use conditions. Preferred topical, oral carriers thus provide the desired characteristics for mouthwashes, mouth rinses, mouth sprays, dental treatment solutions, toothpastes, dental gels, toothpowders, prophylaxis pastes, lozenges, chewing gums, and the like. The topical, oral carriers of the subject invention comprise components typically used in such compositions which are well known to a skilled practitioner. Such components include, but are not limited to, anticaries agents, antiplaque agents, anticalculus agents, dental abrasives, surfactants, flavoring agents, sweetening agents, binders, humectants, thickening agents, buffering agents, preservatives, coloring agents and pigments, ethanol and water.

Water is an optional component of the topical, oral carriers of the compositions of the subject invention. Water employed in the preparation of the commercially suitable compositions should preferably be of low ion content and free of organic impurities. Water preferably comprises from about 2% to about 99%, more preferably from about 20% to about 95% of the compositions of the subject invention. When in the form of toothpaste, the compositions preferably comprise from about 2% to about 45%, more preferably from about 30% to about 40%, water, while mouthwashes comprise preferably from about 45% to about 95%, more preferably from about 75% to about 90%, water.

Dental abrasives useful in the topical, oral carriers of the compositions of the subject invention include many different materials. The material selected must be one which is compatible with the composition of interest and does not excessively abrade dentin. These include, for example, silicas, including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other materials such as those disclosed by Cooley et al. in U.S. Pat. No. 3,070,510, issued Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For this reason they are preferred for use herein.

The silica abrasive polishing materials useful herein, as well as the other abrasives, generally have an average particle size ranging between about 0.1 and 30 microns, preferably between about 5 and 15 microns. The silica abrasive can be precipitated silica or silica gels such as the silica xerogels described in U.S. Pat. No. 3,538,230, issued Mar. 2, 1970 to Pader et al., and in U.S. Pat. No. 3,862,307, issued Jun. 21, 1975 to DiGiulio, both incorporated herein by reference. Preferred are the silica xerogels marketed under the tradename Syloid ® by the W. R. Grace & Company, Davidson Chemical Division. Preferred precipitated silica materials include those marketed by the J. M. Huber Corporation under the tradename, Zeodent ®, particularly the silica carrying the designation Zeodent 119 ®. These silica abrasives are described in U.S. Pat. No. 4,340,583, Wason, issued Jul. 20, 1982, incorporated herein by reference.

Mixtures of abrasives may be used. The amount of abrasive in the compositions described herein ranges from about 6% to about 70%, preferably from about 15% to about 50%, when the dentifrice is a toothpaste. Higher levels, as high as 90%, may be used if the composition is a tooth powder.

Flavoring agents can also be added to the oral compositions of the subject invention to make them more palatable. Suitable flavoring agents include menthol, oil of wintergreen, oil of peppermint, oil of spearmint, oil of sassafras, and oil of clove. Flavoring agents are generally included in the subject compositions in amounts of from about 0% to about 3%, preferably from about 0.04% to about 2% by weight.

Coloring agents may be added to compositions of the subject invention to improve appearance. If present, coloring agents typically are included at levels of from about 0.001% to about 0.5% by weight.

Sweetening agents are also preferred in the compositions of the subject invention to make them more palatable. Sweetening agents which can be used include aspartame, acesulfame, saccharin salts, dextrose, levulose thaumatin, D-tryptophan, dihydrochalcones, and cyclamate salts. Saccharin salts are preferred. Sweetening agents are generally used in the subject compositions in amounts of from about 0% to about 6%, preferably from about 0.005% to about 5% by weight.

Oral compositions can also contain a surfactant. Suitable surfactants are those which are reasonably stable and form suds throughout a wide pH range, including nonsoap anionic, nonionic, cationic, zwitterionic and amphoteric organic synthetic detergents, and compatible mixtures thereof. Many of these suitable surfactants are disclosed in U.S. Pat. No. 4,051,234, issued to Gieske et al. on Sep. 27, 1977, and in U.S. Pat. No. 3,959,458 issued to Agricola, Briner, Granger and Widder on May 25, 1976, both of which are incorporated herein by reference. Surfactants are typically present in compositions of the subject invention at a level of from 0% to about 10%, preferably from about 0.2% to about 4% by weight. Surfactants may also be used as solubilizing agents to help retain sparingly soluble components, e.g., some flavoring agents, in solutions. Surfactants suitable for this purpose include polysorbates and poloxamers.

In preparing oral compositions of the subject invention, it is desirable to add binders and/or thickening agents, particularly to toothpaste compositions. Preferred binders and thickening agents include for example, carboxyvinyl polymers, polysaccharide gums such as xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. These binders and thickening agents are generally present in the compositions of the subject invention in amounts of from about 0% to about 6%, preferably from about 0.1% to about 5% by weight.

Another optional component of the oral carriers of the compositions of the subject invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 2% to about 55%, by weight of the compositions herein. Suitable humectants for use in compositions of the subject invention include edible polyhydric alcohols such as glycerin, sorbitol, xylitol, polyethylene glycol, and propylene glycol, especially sorbitol and glycerin.

Opacifiers may also be used in toothpastes of the subject invention to render the toothpaste opaque. Suitable opacifiers include titanium dioxide and some abrasives including, for example, magnesium aluminum silicate. Opacifiers generally comprise from about 0% to about 4%, preferably from about 0.5% to about 3% by weight of the compositions herein.

Buffering agents are another optional component of the compositions of the subject invention. Suitable buffering agents include any pharmaceutically-acceptable buffers safe for use within the oral cavity with low affinity for aluminum, gallium or indium. Examples of such agents include amino acids such as histidine and glycine, as well as ions of monocarboxylic acids such as acetate and benzoate. The buffering agents serve to retain the pH of the compositions within the preferred range. The amount of buffering agent desirable depends on buffering capacity of the particular agent. Generally the buffering agent comprises from about 0% to about 10%, preferably from about 0.2% to about 5%, by weight of the compositions herein.

Other optional components of the compositions of the subject invention are preservatives. The preservatives prevent microbial growth in the compositions. Suitable preservatives include methylparaben, propylparaben, benzoates and ethanol. If the preservative is ethanol, it generally comprises from 0% to about 35% by weight, preferably from about 5% to about 15%, of the compositions herein. Other preservatives generally comprise from about 0% to about 5% by weight, preferably from about 0.1% to about 2%, of the compositions herein.

Antimicrobial, antiplaque agents can also optionally be present in the oral compositions of the subject invention, on the condition that they are compatible with the Active. Such agents may include, but are not limited to, triclosan, 2,4,4'-trichloro-2'-hydroxydiphenyl ether, as described *The Merck Index*, 11th Ed. (1989), p. 1520 (entry No. 9573); in U.S. Pat. No. 3,506,720; and in Eur. Pat. Appl. No. 0,251,591 of Beecham Group, PLC, published Jan. 7, 1988, chlorohexidine, (*Merck Index*, No. 2090), alexidine (*Merck Index*, No. 222); hexetidine (*Merck Index*, No. 4624); sanguinarine (*Merck Index*, No. 8320); benzalkonium chloride (*Merck Index*, No. 1066); salicylanilide (*Merck Index*, No. 8299); domiphen bromide (*Merck Index*, No. 3411); cetylpyridinium chloride, (CPC) (*Merck Index*, No. 2024); tetradecylpyridinium chloride, (TPC); N-tetradecyl-4-ethypyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as cylium peroxide, hydrogen peroxide, and magnesium monoperthalate and its analogs as described in U.S. Pat. No. 4,670,252; and analogs and salts of the above antimicrobial antiplaque agents. If present, the antimicrobial antiplaque agents may comprise from about 0% to about 6%, preferably from about 0.1% to about 5% by weight of the compositions of the subject invention.

Nutrients can also be present in the oral composition of the subject invention, on condition that they are compatible with the Active. Such agents may include folate, retinoids (Vitamin A), Vitamin C, Vitamin E and zinc. If present, the nutrients generally comprise from about 0.001% to about 10% by weight of the compositions of the subject invention.

Compositions of the subject invention may also include one or more anticalculus agents, on the condition that they are compatible with the Active. Anticalculus agents which may be useful in the compositions of the subject invention include zinc. Preferred compounds to deliver the zinc are sodium zinc citrate and zinc chloride. The anticalculus agents generally comprise from about 0% to about 15%, preferably from about 0.2% to about 13%, more preferably from about 0.4% to about 6% of the compositions of the subject invention.

Preferred compositions of the subject invention are in the form of dentifrices. Components of toothpastes generally include a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%).

Other preferred compositions of the subject invention are mouthwashes and mouth sprays. Components of such mouthwashes and mouth sprays include water (from about 45% to about 95%), ethanol (from about 0% to about 25%), humectant (from about 0% to about 50%), surfactant agent (from about 0.01% to about 7%), flavoring agent (from about 0.04% to about 2%), sweetening agent (from about 0.1% to about 3%), and coloring agent (from about 0.001% to about 0.5%). Such mouthwashes and mouth sprays may also include one or more of an anticalculus agent (from about 0.1% to about 3%), and an antiplaque agent (from about 0.1% to about 5%).

Other preferred compositions of the subject invention are dental solutions. Components of such dental solutions generally include water (from about 90% to about 99%), preservative (from about 0.01% to about 0.5%), thickening agent (from about 0% to about 5%), flavoring agent (from about 0.04% to about 2%), sweetening agent (from about 0.1% to about 3%), and surfactant (from about 0% to about 5%).

Oral gel compositions typically include one or more of water (from about 0% to about 99%), a humectant such as glycerin (from 0% to about 99%), a thickening agent (from about 0.1% to about 5%), a flavoring agent (from about 0.04% to about 2%), and a sweetening agent (from about 0.01% to about 0.5%).

Chewing gum compositions typically include one or more of a gum base (from about 50% to about 99%), a flavoring agent (from about 0.04% to about 2%) and a sweetening agent (from about 0.01% to about 20%).

Lozenge compositions typically include a lozenge carrier comprising one or more of a candy base (from about 50% to about 99%), a flavoring agent (from about 0.001% to about 2%, and a coloring agent (from about 0.001% to about 0.5%). Examples of suitable lozenge carriers are disclosed in U.S. Pat. No. 4,931,473 issued Jun. 5, 1990 to Kelleher et al., and in U.S. Pat. No. 4,927,634 issued May 22, 1990 to Sorrentino et al., both incorporated herein by reference.

The pH of the subject compositions and/or its pH in the mouth can be any pH which is safe for the mouth's hard and soft tissues. Such pH's are generally from about 3 to about 7, more preferably from about 4 to about 7, more preferably still from about 4.5 to about 6.5.

Methods of Use

Another aspect of the subject invention involves methods for reducing or preventing dental plaque or gingivitis, by application of compositions comprising a safe and effective amount of Active, to tissues of the oral cavity. Such compositions are described hereinabove.

These methods involve administering a safe and effective amount of Active typically by administering an oral composition of the subject invention, as described hereinabove to the oral cavity. Generally an amount of at least about 0.05 g of the Active compound is effective. The teeth and other oral cavity tissues are "bathed" in the Active.

When the oral composition is a toothpaste, typically from about 0.3 grams to about 15 grams, preferably from about 0.5 grams to about 5 grams, more preferably from about 1 to about 2 grams, of toothpaste is applied to an applicating device e.g., a toothbrush. The applicating device is then contacted with the oral cavity surfaces in a manner such that the oral composition is contacted with tissue of the oral cavity, especially the teeth and gums. The applicating device may be further used to effect an even distribution of the oral composition to the tooth surface, for example by brushing. The application preferably lasts for a period of from about 15 seconds to about 10 minutes, more preferably from about 1 minute to about 2 minutes. Following application, the toothpaste residue is typically removed from the tooth surface by using a liquid acceptable to the oral cavity, typically water, to rinse the oral cavity.

When the oral composition is a mouthwash, typically from about 1 ml. to about 20 ml., preferably from about 2 ml. to about 15 ml., most preferably from about 10 ml. to about 15 ml., of liquid mouthwash containing the antiplaque Active is introduced to the oral cavity. The liquid mouthwash is then agitated for from about 10 seconds to about 30 min., preferably from about 15 seconds to about 3 min., more preferably from about 60 seconds to about 2 minutes, within the oral cavity to obtain an improved distribution of the mouthwash over the tissue of the oral cavity. Following agitation, the mouthwash is typically expectorated from the oral cavity.

Application frequency is preferably from about once daily to about 4 times daily, more preferably from about 3 times weekly to about 3 times daily, more preferably still from about once to about twice daily. The period of such treatment typically ranges from about one day to a lifetime.

ORAL COMPOSITION EXAMPLES

The following non-limiting examples further describe and demonstrate preferred embodiments within the scope of the subject invention. The examples are given solely for illustration and are not to be construed as limitations of the subject invention as many variations are possible without departing from the spirit and scope of the subject invention.

The compositions of the subject invention can be made using methods which are common in the oral products area.

Example I

The following is an example of a mouth rinse formulation and is made using conventional processes.

| Component | Wt % |
| --- | --- |
| Sorbitol (70% aq) | 18.000 |
| NaSaccharin | 0.040 |
| F&DC Blue #1 | 0.070 |
| Ethanol | 8.500 |
| Spearmint Flavor | 0.118 |
| Tween 80 | 0.472 |
| Pluronic F127 | 0.157 |
| N-acetyl-L-glutamine aluminum salt | 1.000 |
| NaOH (1N) | 4.507 |
| Water | q.s. |

Example II

The following is an example of a dentifrice formulation.

| Component | Wt % |
| --- | --- |
| Sorbitol (70% aq) | 49.500 |
| NaSaccharin | 0.350 |
| Dye Solution | 0.400 |
| Precipitated Silica (J.M. Huber, Inc.) | 20.000 |
| Flavor | 1.300 |
| Sodium Alkyl Sulfate (27.9% solution) | 5.000 |
| Carbopol 940S (B.F. Goodrich) | 0.200 |
| Xanthan Gum (Kelco Inc.) | 0.600 |
| N-acetyl-L-glutamine aluminum salt | 3.000 |
| Sodium Hydroxide | 0.066 |
| Water | q.s. |

The above composition is made by combining the water and part of the sorbitol in an agitated mixture and heating this mixture to about 25° C. (room temperature). The saccharin, N-acetyl-L-glutamine aluminum salt, and precipitated silica are then added in order and the total mixture is mixed for from 5 to 10 minutes. The flavor, dye, and surfactant are then added. In a separate vessel the remaining sorbitol, the Carbopol and the xantham gum are slurried together and added to the main tank. After 10 minutes of mixing the NaOH is added to adjust the pH. The complete batch is mixed at 70° C. for one-half hour, then milled and deaerated.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method for reducing or preventing dental plaque, or gingival or periodontal diseases comprising contacting tooth surfaces within the oral cavity in humans or lower animals with a composition comprising a safe and effective amount of a complex of metal ions with N-acetylated amino acids wherein the amino acids are selected from the group consisting of naturally occurring amino acids and wherein the metal ions are selected from the group consisting of $In^{3+}$, $Ga^{3+}$, and $Al^{3+}$; and a pharmaceutically-acceptable topical oral carrier which comprises a pharmaceutically-acceptable dental abrasive.

2. The method of claim 1 for reducing or preventing dental plaque.

3. The method of claim 2 wherein the amino acid is glutamine or cysteine.

4. The method of claim 3 wherein the amino acid is glutamine.

5. The method of claim 3 wherein the amino acid is cysteine.

6. The method of claim 3 wherein the metal ion is $Al^{3+}$.

7. The method of claim 6 wherein the composition comprises from about 0.05% to about 10% by weight of the complex.

8. The method of claim 7 wherein the composition comprises about 0.1% to about 5% of the complex.

9. The method of claim 7 wherein the pH of the composition is from about 3 to about 7.

10. The method of claim 8 wherein the pH of the composition is from about 4 to about 7.

11. An oral care composition for reducing or preventing dental plaque, or gingival or periodontal diseases comprising a safe and effective amount of a complex of metal ions with N-acetylated amino acids wherein the amino acids are selected from the group consisting of naturally occurring amino acids and wherein the metal ions are selected from the group consisting of $In^{3+}$, $Ga^{3+}$, and $Al^{3+}$; and a pharmaceutically-acceptable topical oral carrier which comprises a pharmaceutically-acceptable dental abrasive.

12. The oral care composition of claim 11 wherein the amino acid is glutamine or cysteine.

13. The oral care composition of claim 12 wherein the amino acid is glutamine.

14. The oral care composition of claim 12 wherein the amino acid is cysteine.

15. The oral care composition of claim 12 wherein the metal ion is $Al^{3+}$.

16. The oral care composition of claim 15 wherein the composition comprises from about 0.05% to about 10% by weight of the complex.

17. The oral care composition of claim 16 wherein the composition comprises about 0.1% to about 5% of the complex.

18. The oral care composition of claim 16 wherein the pH of the composition is from about 3 to about 7.

19. The oral care composition of claim 18 wherein the pH of the composition is from about 4 to about 7.

20. The oral care composition of claim 19 wherein the pH of the composition is from about 4.5 to about 6.5.

* * * * *